United States Patent
Davidson

(10) Patent No.: US 10,524,645 B2
(45) Date of Patent: Jan. 7, 2020

(54) METHOD AND SYSTEM FOR ELIMINATING IMAGE MOTION BLUR IN A MULTIPLE VIEWING ELEMENTS ENDOSCOPE

(71) Applicant: EndoChoice, Inc., Alpharetta, GA (US)

(72) Inventor: Tal Davidson, Yokneam Ilit (IL)

(73) Assignee: EndoChoice, Inc., Alpharetta, GA (US)

( * ) Notice: Subject to any disclaimer, the term of this patent is extended or adjusted under 35 U.S.C. 154(b) by 809 days.

(21) Appl. No.: 14/604,494

(22) Filed: Jan. 23, 2015

(65) Prior Publication Data

US 2015/0208909 A1   Jul. 30, 2015

Related U.S. Application Data

(60) Provisional application No. 61/931,563, filed on Jan. 25, 2014.

(51) Int. Cl.
*A61B 1/045* (2006.01)
*A61B 1/06* (2006.01)

(52) U.S. Cl.
CPC ............ *A61B 1/045* (2013.01); *A61B 1/0684* (2013.01)

(58) Field of Classification Search
CPC ... A61B 1/00006; A61B 1/045; A61B 1/0676; A61B 1/0684; H04N 5/23264; H04N 5/23267; H04N 5/2327; H04N 5/236
See application file for complete search history.

(56) References Cited

U.S. PATENT DOCUMENTS 3,639,714 A   2/1972 Fujimoto
3,955,064 A   5/1976 Demetrio
(Continued)

FOREIGN PATENT DOCUMENTS

CA   2297986   3/1999
CA   2765559   12/2010
(Continued)

OTHER PUBLICATIONS

Notice of Allowance dated May 25, 2017 for U.S. Appl. No. 14/318,189.
(Continued)

*Primary Examiner* — Timothy J Neal
*Assistant Examiner* — Jae Woo
(74) *Attorney, Agent, or Firm* — Bookoff McAndrews, PLLC

(57) ABSTRACT

In a multiple viewing elements endoscope, fuzziness and blur in the images due to movement of the endoscope is reduced by using flashing illuminators instead of continuous illumination. In one embodiment, LED illuminators are flashed at high intensity and for a very short duration. To address interlacing artifacts, LEDs are flashed once at the end of a field and again at the beginning of the following field to minimize the time difference between the capture of the two fields. In another embodiment, the LEDs are flashed once wherein the single flash overlaps the end of a field and the beginning of the following field. In some embodiments, still images may be captured with fine detail by pressing a button on the endoscope handle which activates the LEDs to flash along with the capture of an image. In one embodiment, pressing a button for still image capture results in the capture of two fields, each accompanied by a flash, which are interlaced to form a single still image frame.

9 Claims, 8 Drawing Sheets

(56) References Cited

U.S. PATENT DOCUMENTS

| | | | |
|---|---|---|---|
| 4,027,697 | A | 6/1977 | Bonney |
| 4,037,588 | A | 7/1977 | Heckele |
| 4,084,401 | A | 4/1978 | Belardi |
| 4,402,313 | A | 9/1983 | Yabe |
| 4,461,282 | A | 7/1984 | Ouchi |
| 4,494,549 | A | 1/1985 | Namba |
| 4,532,918 | A | 8/1985 | Wheeler |
| 4,588,294 | A | 5/1986 | Siegmund |
| 4,641,635 | A | 2/1987 | Yabe |
| 4,646,724 | A * | 3/1987 | Sato ............ A61B 1/042 348/68 |
| 4,710,807 | A * | 12/1987 | Chikama ......... A61B 1/05 348/371 |
| 4,727,859 | A | 3/1988 | Lia |
| 4,740,837 | A * | 4/1988 | Yanagisawa ....... A61B 1/05 348/211.99 |
| 4,743,966 | A * | 5/1988 | Matsuo ........... A61B 1/05 348/216.1 |
| 4,764,001 | A | 8/1988 | Yokota |
| 4,801,792 | A | 1/1989 | Yamasita |
| 4,825,850 | A | 5/1989 | Opie |
| 4,877,314 | A | 10/1989 | Kanamori |
| 4,902,115 | A | 2/1990 | Takahashi |
| 4,953,539 | A * | 9/1990 | Nakamura ........ A61B 1/00177 348/E5.029 |
| 4,976,522 | A | 12/1990 | Igarashi |
| 4,979,497 | A * | 12/1990 | Matsuura ........ A61B 1/00068 348/65 |
| 4,984,878 | A | 1/1991 | Miyano |
| 5,007,406 | A | 4/1991 | Takahashi |
| 5,007,407 | A * | 4/1991 | Kikuchi ........... A61B 1/042 348/68 |
| 5,014,685 | A | 5/1991 | Takahashi |
| 5,193,525 | A | 3/1993 | Silverstein |
| 5,224,929 | A | 7/1993 | Remiszewski |
| 5,296,971 | A | 3/1994 | Mori |
| 5,331,949 | A * | 7/1994 | Funakoshi ........ A61B 1/042 348/221.1 |
| 5,359,456 | A | 10/1994 | Kikuchi |
| 5,395,329 | A | 3/1995 | Fleischhacker |
| 5,408,263 | A * | 4/1995 | Kikuchi ......... A61B 1/00059 348/223.1 |
| 5,447,148 | A | 9/1995 | Oneda |
| 5,460,167 | A | 10/1995 | Yabe |
| 5,464,007 | A | 11/1995 | Krauter |
| 5,475,420 | A | 12/1995 | Buchin |
| 5,489,256 | A | 2/1996 | Adair |
| 5,518,501 | A | 5/1996 | On |
| 5,518,502 | A | 5/1996 | Kaplan |
| 5,547,455 | A | 8/1996 | McKenna |
| 5,547,457 | A | 8/1996 | Tsuyuki |
| 5,575,755 | A | 11/1996 | Krauter |
| 5,587,839 | A | 12/1996 | Miyano |
| 5,630,782 | A | 5/1997 | Adair |
| 5,630,798 | A | 5/1997 | Beiser |
| 5,662,588 | A | 9/1997 | Iida |
| 5,674,182 | A | 10/1997 | Suzuki |
| 5,685,821 | A | 11/1997 | Pike |
| 5,685,823 | A | 11/1997 | Ito |
| 5,702,347 | A | 12/1997 | Yabe |
| 5,707,344 | A | 1/1998 | Nakazawa |
| 5,725,474 | A | 3/1998 | Yasui |
| 5,725,476 | A | 3/1998 | Yasui |
| 5,725,477 | A | 3/1998 | Yasui |
| 5,725,478 | A | 3/1998 | Saad |
| 5,777,797 | A | 7/1998 | Miyano |
| 5,782,751 | A | 7/1998 | Matsuno |
| 5,800,341 | A | 9/1998 | McKenna |
| 5,810,715 | A | 9/1998 | Moriyama |
| 5,810,717 | A | 9/1998 | Maeda |
| 5,810,770 | A | 9/1998 | Chin |
| 5,830,121 | A | 11/1998 | Enomoto |
| 5,836,894 | A | 11/1998 | Sarvazyan |
| 5,860,913 | A | 1/1999 | Yamaya |
| 5,870,234 | A | 2/1999 | Ebbesmeier nee Schitthof |
| 5,916,148 | A | 6/1999 | Tsuyuki |
| 5,940,126 | A | 8/1999 | Kimura |
| 6,058,109 | A | 5/2000 | Lechleider |
| 6,095,970 | A | 8/2000 | Hidaka |
| 6,095,971 | A | 8/2000 | Takahashi |
| 6,117,068 | A | 9/2000 | Gourley |
| 6,181,481 | B1 | 1/2001 | Yamamoto |
| 6,196,967 | B1 | 3/2001 | Lim |
| 6,234,959 | B1 * | 5/2001 | Higuchi ........... A61B 1/05 348/69 |
| 6,261,226 | B1 | 7/2001 | McKenna |
| 6,277,064 | B1 | 8/2001 | Yoon |
| 6,359,674 | B1 | 3/2002 | Horiuchi |
| 6,375,610 | B2 | 4/2002 | Verschuur |
| 6,402,738 | B1 | 6/2002 | Ouchi |
| 6,419,626 | B1 | 7/2002 | Yoon |
| 6,476,851 | B1 | 11/2002 | Nakamura |
| 6,520,908 | B1 | 2/2003 | Ikeda |
| 6,636,254 | B1 | 10/2003 | Onishi |
| 6,638,214 | B2 | 10/2003 | Akiba |
| 6,673,012 | B2 | 1/2004 | Fujii |
| 6,690,337 | B1 | 2/2004 | Mayer, III |
| 6,712,760 | B2 | 3/2004 | Sano |
| 6,832,984 | B2 | 12/2004 | Stelzer |
| 6,888,119 | B2 | 5/2005 | Iizuka |
| 6,997,871 | B2 | 2/2006 | Sonnenschein |
| 7,154,378 | B1 | 12/2006 | Ertas |
| 7,435,218 | B2 | 10/2008 | Krattiger |
| 7,621,869 | B2 | 11/2009 | Ratnakar |
| 7,630,148 | B1 | 12/2009 | Yang |
| 7,701,650 | B2 | 4/2010 | Lin |
| 7,713,246 | B2 | 5/2010 | Shia |
| 7,746,572 | B2 | 6/2010 | Asami |
| 7,813,047 | B2 | 10/2010 | Wang |
| 7,828,725 | B2 | 11/2010 | Maruyama |
| 7,918,788 | B2 | 4/2011 | Lin |
| 7,927,272 | B2 | 4/2011 | Bayer |
| 7,967,745 | B2 | 6/2011 | Gilad |
| 7,976,462 | B2 | 7/2011 | Wright |
| 8,064,666 | B2 | 11/2011 | Bayer |
| 8,182,422 | B2 | 5/2012 | Bayer |
| 8,190,016 | B2 * | 5/2012 | Pozniansky ........ H04N 5/2354 396/153 |
| 8,197,399 | B2 | 6/2012 | Bayer |
| 8,235,887 | B2 | 8/2012 | Bayer |
| 8,262,558 | B2 | 9/2012 | Sato |
| 8,287,446 | B2 | 10/2012 | Bayer |
| 8,289,381 | B2 | 10/2012 | Bayer |
| 8,300,325 | B2 | 10/2012 | Katahira |
| 8,310,530 | B2 | 11/2012 | Bayer |
| 8,353,860 | B2 | 1/2013 | Boulais |
| 8,447,132 | B1 | 5/2013 | Galil |
| 8,449,457 | B2 | 5/2013 | Aizenfeld |
| 8,460,182 | B2 | 6/2013 | Ouyang |
| 8,585,584 | B2 | 11/2013 | Ratnakar |
| 8,587,645 | B2 | 11/2013 | Bayer |
| 8,672,836 | B2 | 3/2014 | Higgins |
| 8,715,168 | B2 | 5/2014 | Ratnakar |
| 8,797,392 | B2 | 8/2014 | Bayer |
| 8,872,906 | B2 | 10/2014 | Bayer |
| 8,926,502 | B2 | 1/2015 | Levy |
| 9,044,185 | B2 | 6/2015 | Bayer |
| 9,101,266 | B2 | 8/2015 | Levi |
| 9,101,268 | B2 | 8/2015 | Levy |
| 9,101,287 | B2 | 8/2015 | Levy |
| 9,144,664 | B2 | 9/2015 | Jacobsen |
| 9,289,110 | B2 | 3/2016 | Woolford |
| 9,314,147 | B2 | 4/2016 | Levy |
| 9,320,419 | B2 | 4/2016 | Kirma |
| 2001/0036322 | A1 | 11/2001 | Bloomfield |
| 2002/0017515 | A1 | 2/2002 | Obata |
| 2002/0047897 | A1 | 4/2002 | Sugimoto |
| 2002/0087047 | A1 | 7/2002 | Remijan |
| 2002/0109771 | A1 | 8/2002 | Ledbetter |
| 2002/0109774 | A1 | 8/2002 | Meron |
| 2002/0161279 | A1 | 10/2002 | Luloh |
| 2002/0161281 | A1 | 10/2002 | Jaffe |
| 2002/0172498 | A1 | 11/2002 | Esenyan |

(56) References Cited

U.S. PATENT DOCUMENTS

| | | |
|---|---|---|
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2003/0215767 A1* | 11/2003 | Taub ................ A61B 1/0607 433/29 |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Boutillette |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | Delorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0036743 A1* | 2/2009 | Yabe ................ A61B 1/00009 600/180 |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2010/0326703 A1 | 12/2010 | Gilad |
| 2011/0004058 A1 | 1/2011 | Oneda |
| 2011/0004059 A1 | 1/2011 | Arneson |

(56) References Cited

U.S. PATENT DOCUMENTS

| | | |
|---|---|---|
| 2011/0034769 A1 | 2/2011 | Adair |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0251454 A1* | 10/2011 | Robb ............... A61B 1/31 600/103 |
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0053642 A1* | 2/2013 | Mizuyoshi ......... A61B 1/00006 600/109 |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0113970 A1* | 5/2013 | Laser ............... A61B 1/00052 348/308 |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0128685 A1* | 5/2014 | Na .................. A61N 1/30 600/249 |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |

(56) References Cited

FOREIGN PATENT DOCUMENTS

| | | |
|---|---|---|
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 | 12/2010 |
| WO | 2012038958 | 3/2012 |
| WO | 2012056453 | 5/2012 |
| WO | 2012075153 A2 | 6/2012 |
| WO | 2012077116 | 6/2012 |
| WO | 2012077117 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

Office Action dated May 23, 2017 for U.S. Appl. No. 14/500,975.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.
International Search Report for PCT/US2015/012751, dated Jun. 26, 2015.
International Search Report for PCT/US14/37004, dated Sep. 25, 2014.
International Search Report for PCT/US2014/037526, dated Oct. 16, 2014.
International Search Report for PCT/US14/38094, dated Nov. 6, 2014.
International Search Report for PCT/US2014/58143, dated Jan. 21, 2015.
International Search Report for PCT/US2014/071085, dated Mar. 27, 2015.
International Search Report for PCT/US2015/027902, dated Jul. 23, 2015.
International Search Report for PCT/US2015/012506, dated Dec. 11, 2015.
International Search Report for PCT/US2015/29421, dated Aug. 7, 2015.
International Search Report for PCT/US2015/28962, dated Jul. 28, 2015.
International Search Report for PCT/US2015/47334, dated Dec. 28, 2015.
International Search Report for PCT/US2015/41396, dated Sep. 29, 2015.
International Search Report for PCT/US2015/66486, dated Dec. 17, 2015.
International Search Report for PCT/US2015/6548, dated Feb. 26, 2016.
Office Action dated Feb. 26, 2016 for U.S. Appl. No. 14/274,323.
Office Action dated Feb. 4, 2016 for U.S. Appl. No. 14/271,234.
Office Action dated Jun. 30, 2016 for U.S. Appl. No. 13/655,120.
Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Hear, Plastics Technology, Jun. 2001—article obtained online from http://www.ptonline.com/articles/plastics-that-conduct-heat.
Office Action dated Aug. 11, 2016 for U.S. Appl. No. 14/318,249.

(56) References Cited

OTHER PUBLICATIONS

Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20, 2017 for U.S. Appl. No. 14/278,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Notice of Allowance dated Apr. 12, 2017 for U.S. Appl. No. 14/603,137.
Notice of Allowance dated Apr. 18, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/988,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.

\* cited by examiner

METHOD AND SYSTEM FOR ELIMINATING IMAGE MOTION BLUR IN A MULTIPLE VIEWING ELEMENTS ENDOSCOPE

CROSS-REFERENCE TO RELATED APPLICATIONS

The present application relies on, for priority, U.S. Provisional Patent Application No. 61/931,563, entitled "Method and System For Eliminating Image Motion Blur In A Multi-Viewing Element Endoscope" and filed on Jan. 25, 2014.

In addition, the present application is related to the following applications: U.S. patent application Ser. No. 13/655,120, entitled "Multi-Camera Endoscope" and filed on Oct. 18, 2012; U.S. patent application Ser. No. 13/212,627, entitled "Multi-Viewing Element Endoscope" and filed on Aug. 18, 2011; and U.S. patent application Ser. No. 13/190,968, entitled "Multi-Camera Endoscope" and filed on Jul. 26, 2011, all of which are continuation-in-part applications of U.S. patent application Ser. No. 13/119,032, entitled "Multi-Camera Endoscope" and filed on Jul. 15, 2011, which is a National Stage Entry of PCT Application Number PCT/IL2010/000476, of the same title and filed on Jun. 16, 2010, which, in turn, relies upon U.S. Provisional Patent Application No. 61/218,085, filed on Jun. 18, 2009, for priority.

The present application is also related to the following applications: U.S. patent application Ser. No. 13/882,004, entitled "Optical Systems for Multi-Sensor Endoscopes" and filed on May 23, 2013, which is a National Stage Entry of PCT Application Number PCT/IL11/00832, of the same title and filed on Oct. 27, 2011, which, in turn, relies upon U.S. Provisional Patent Application No. 61/407,495, of the same title and filed on Oct. 28, 2010, for priority; and U.S. patent application Ser. No. 14/263,896, entitled "Video Processing In A Compact Multi-Viewing Element Endoscope System" and filed on Apr. 28, 2014, which relies on U.S. Provisional Patent Application No. 61/817,237, entitled "Method and System for Video Processing in a Multi-Viewing Element Endoscope", and filed on Apr. 29, 2013, for priority.

All of the above referenced applications are herein incorporated by reference in their entirety.

FIELD

The present specification relates generally to an endoscope with multiple viewing elements, and more specifically, to a method and system for eliminating blur in images created during the movement of the endoscope during an endoscopic procedure.

BACKGROUND

Endoscopes have attained great acceptance within the medical community since they provide a means for performing procedures with minimal patient trauma while enabling the physician to view the internal anatomy of the patient. Over the years, numerous endoscopes have been developed and categorized according to specific applications, such as cystoscopy, colonoscopy, laparoscopy, and upper gastrointestinal (GI) endoscopy, among others. Endoscopes may be inserted into the body's natural orifices or through an incision in the skin.

An endoscope typically comprises an elongated tubular shaft, rigid or flexible, having a video camera, also referred to as a viewing element, and a light source, such as a fiber optic light source or Light Emitting Diode (LED), at its distal end. The shaft is connected to a handle which sometimes includes an ocular or eyepiece for direct viewing. Viewing is also usually possible via an external screen. Various surgical tools may be inserted through a working channel in the endoscope for performing different surgical procedures.

There are known various endoscopes that employ optical heads, in their front insertion part, for viewing the interior of a body cavity or lumen, such as the lower digestive track. Such optical heads normally include at least an illumination means for illuminating the object, an objective lens system and a sensor array.

As light is emitted continuously from the source of illumination, it results in fuzzy or blurred images during the movement of the scope. Further, interlaced video can show significant horizontal line artifacts during scope movement, thereby reducing vertical resolution of the video being displayed.

Since the movement of scope is inevitable during an endoscopic procedure, blurred or fuzzy images may not allow a physician to analyze an area under inspection in full detail. Fuzzy images and reduced vertical resolution considerably reduce fine detail, which may have important clinical significance. This in turn affects the rate of detection of pathological objects that exist in the body cavity in which the endoscope operates. For example, clinical literature shows that the average adenoma miss rate is over 24%. That is, detection of cancer is missed in more than 24 of every 100 patients. Further, from a medical industry viewpoint, unless a physician is correctly identifying cancer in at least 20% of cancer patients, the average miss rate is considered higher than industry standards.

Therefore, there is a need in the art for endoscopes that provide high image quality during endoscopic procedures, even when the endoscope is moving through the lumen at a fast pace, thereby ensuring better analysis and detection of medical conditions.

SUMMARY

In a multiple viewing elements endoscope, fuzziness and blur in the images due to movement of the endoscope is reduced by using flashing illuminators instead of continuous illumination. In one embodiment, LED illuminators are flashed at high intensity and for a very short duration. To address interlacing artifacts, LEDs are flashed once at the end of a field and again at the beginning of the following field to minimize the time difference between the capture of the two fields and produce a frame that combines the two fields without noticeable artifacts. In another embodiment, the LEDs are flashed once wherein the single flash overlaps the end of a field and the beginning of the following field.

In some embodiments, a button on the endoscope handle may be used to manually activate the LEDs to flash along with the capture of an image, to capture still images with fine detail.

The present specification discloses an endoscope system comprising: an endoscope having a tip; one or more viewing elements positioned in said tip, wherein each viewing element comprises an image sensor and lens assembly; one or more discrete illuminators positioned in said tip to illuminate the fields of view of said viewing elements; and a controller external to said endoscope for concurrently controlling the viewing elements and the illuminators, wherein the controller is configured to flash the illuminators in a pair of flashes for a pre-set duration relative to a single interlaced image frame comprising a first integration frame having a first length, a first beginning, and a first end and a second integration frame having a second length, a second beginning, and a second end, wherein a first flash of said pair of flashes is configured to have a first pre-set duration beginning after said first beginning and ending before or at said first end of said first integration frame and wherein a second flash of said pair of flashes is configured to a have a second pre-set duration beginning at or after said second beginning and ending before said second end of said second integration frame.

The at least one discrete illuminator may comprise light emitting diodes (LEDs), optic fibers, or a combination of LEDs and optic fibers.

The first length of said first integration frame and said second length of said second integration frame may each range from approximately 1/120 sec to 1/30 sec and said first pre-set duration of said first flash and said second pre-set duration of said second flash may each range from approximately 1/1000 sec to 1/60 sec.

Optionally, said first length of said first integration frame and said second length of said second integration frame are each equal to approximately 1/60 sec and said first pre-set duration of said first flash and said second pre-set duration of said second flash are each equal to approximately 1/125 sec.

Optionally, the endoscope further comprises a handle with buttons for controlling functions of said endoscope wherein a button on the endoscope handle may be pressed to flash the illuminators and capture a still image. Optionally, pressing the button for still image capture results in the capture of two image fields that are each accompanied by a flash.

The controller may further comprise: a camera board for controlling power supply to the illuminators and controlling the operation of the image sensors of the viewing elements; and a Field Programmable Gate Array (FPGA) in communication with the camera board for performing logical tasks implemented by hardware and logical tasks related to video image processing.

The present specification also discloses an endoscope system comprising: an endoscope having a tip; one or more viewing elements positioned in said tip, wherein each viewing element comprises an image sensor and lens assembly; one or more discrete illuminators positioned in said tip to illuminate the fields of view of said viewing elements; and a controller external to said endoscope for concurrently controlling the viewing elements and the illuminators, wherein the controller is configured to flash the illuminators in a single flash for a pre-set duration relative to a single interlaced image frame comprising a first integration frame having a first length, a first beginning, and a first end and a second integration frame having a second length, a second beginning, and a second end, wherein said single flash is configured to have a pre-set duration beginning after said first beginning of said first integration frame and ending before said second end of said second integration frame and being shorter than a combined total of said first length of said first integration frame and second length of said second integration frame, further wherein said pre-set duration comprises equal parts of said first length and second length.

The at least one discrete illuminator may comprise light emitting diodes (LEDs), optic fibers, or a combination of LEDs and optic fibers.

The first length of said first integration frame and said second length of said second integration frame may each range from approximately 1/120 sec to 1/30 sec and said pre-set duration of said single flash ranges from approximately 1/1000 sec to 1/30 sec.

Optionally, said first length of said first integration frame and said second length of said second integration frame are each equal to approximately 1/60 sec and said pre-set duration of said single flash is equal to approximately 1/60 sec.

Optionally, the endoscope further comprises a handle with buttons for controlling functions of said endoscope wherein a button on the endoscope handle may be pressed to flash the illuminators and capture a still image. Optionally, pressing the button for still image capture results in the capture of two image fields that are each accompanied by a flash.

The controller may further comprise: a camera board for controlling power supply to the illuminators and controlling the operation of the image sensors of the viewing elements; and a Field Programmable Gate Array (FPGA) in communication with the camera board for performing logical tasks implemented by hardware and logical tasks related to video image processing.

The present specification also discloses a method of reducing blur or noise in an image generated by an endoscope system, comprising the steps of: providing an endoscope system comprising an endoscope having a tip; one or more viewing elements positioned in said tip, wherein each viewing element comprises an image sensor and lens assembly; one or more discrete illuminators positioned in said tip to illuminate the fields of view of said viewing elements; and a controller external to said endoscope for concurrently controlling the viewing elements and the illuminators, wherein the controller is configured to flash the illuminators in a pair of flashes for a pre-set duration relative to a single interlaced image frame comprising a first integration frame having a first length, a first beginning, and a first end and a second integration frame having a second length, a second beginning, and a second end, wherein a first flash of said pair of flashes is configured to have a first pre-set duration beginning after said first beginning and ending at said first end of said first integration frame and being shorter than said first length of said first integration frame and wherein a second flash of said pair of flashes is configured to a have a second pre-set duration beginning at said second beginning and ending before said second end of said second integration frame and being shorter than said second length of said second integration frame; setting said first pre-set duration of said first flash to half of said first length to begin half way through said first integration frame and end at said first end of said first integration frame, and setting said second pre-set duration of said second flash to half of said second length to begin at said second beginning and end half way through said second integration frame; evaluating said single interlaced image frame for blur or noise; reducing said first pre-set duration such that said first flash begins later than the previous first flash began and still ends at the end of said first integration frame and reducing said second pre-set duration such that said second flash still begins with said second integration frame but ends before the previous second flash ended to reduce or eliminate blur; increasing said first pre-set duration such that said first flash begins before the previous first flash began and still ends at the end of said first integration frame and increasing said second pre-set duration such that said second flash still begins with said second integration frame but ends after the previous second flash ended to reduce or eliminate noise; and applying said first pre-set duration to all following first flashes and said second pre-set duration to all following second flashes once blur and noise have been satisfactorily reduced or eliminated.

The present specification also discloses a method of reducing blur or noise in an image generated by an endoscope system, comprising the steps of: providing an endoscope system comprising an endoscope having a tip; one or more viewing elements positioned in said tip, wherein each viewing element comprises an image sensor and lens assembly; one or more discrete illuminators positioned in said tip to illuminate the fields of view of said viewing elements; and a controller external to said endoscope for concurrently controlling the viewing elements and the illuminators, wherein the controller is configured to flash the illuminators in a single flash for a pre-set duration relative to a single interlaced image frame comprising a first integration frame having a first length, a first beginning, and a first end and a second integration frame having a second length, a second beginning, and a second end, wherein said single flash is configured to have a pre-set duration beginning after said first beginning of said first integration frame and ending before said second end of said second integration frame and being shorter than a combined total of said first length of said first integration frame and second length of said second integration frame, further wherein said pre-set duration comprises equal parts of said first length and second length; setting said pre-set duration of said single flash to half of said first length of said first integration frame plus half of said second length of said second integration frame to begin half way through said first integration frame and end half way through said second integration frame; evaluating said single interlaced image frame for blur or noise; reducing said pre-set duration such that said single flash begins later than the previous single flash began but still begins within said first integration frame and ends before the previous single flash ended but still ends within said second integration frame to reduce or eliminate blur; increasing said pre-set duration such that said single flash begins before the previous single flash began but still begins within said first integration frame and ends after the previous single flash ended but still ends within said second integration frame to reduce or eliminate noise; and applying said pre-set duration to all following single flashes once blur and noise have been satisfactorily reduced or eliminated.

The aforementioned and other embodiments of the present shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein.

DETAILED DESCRIPTION

Figure 1:
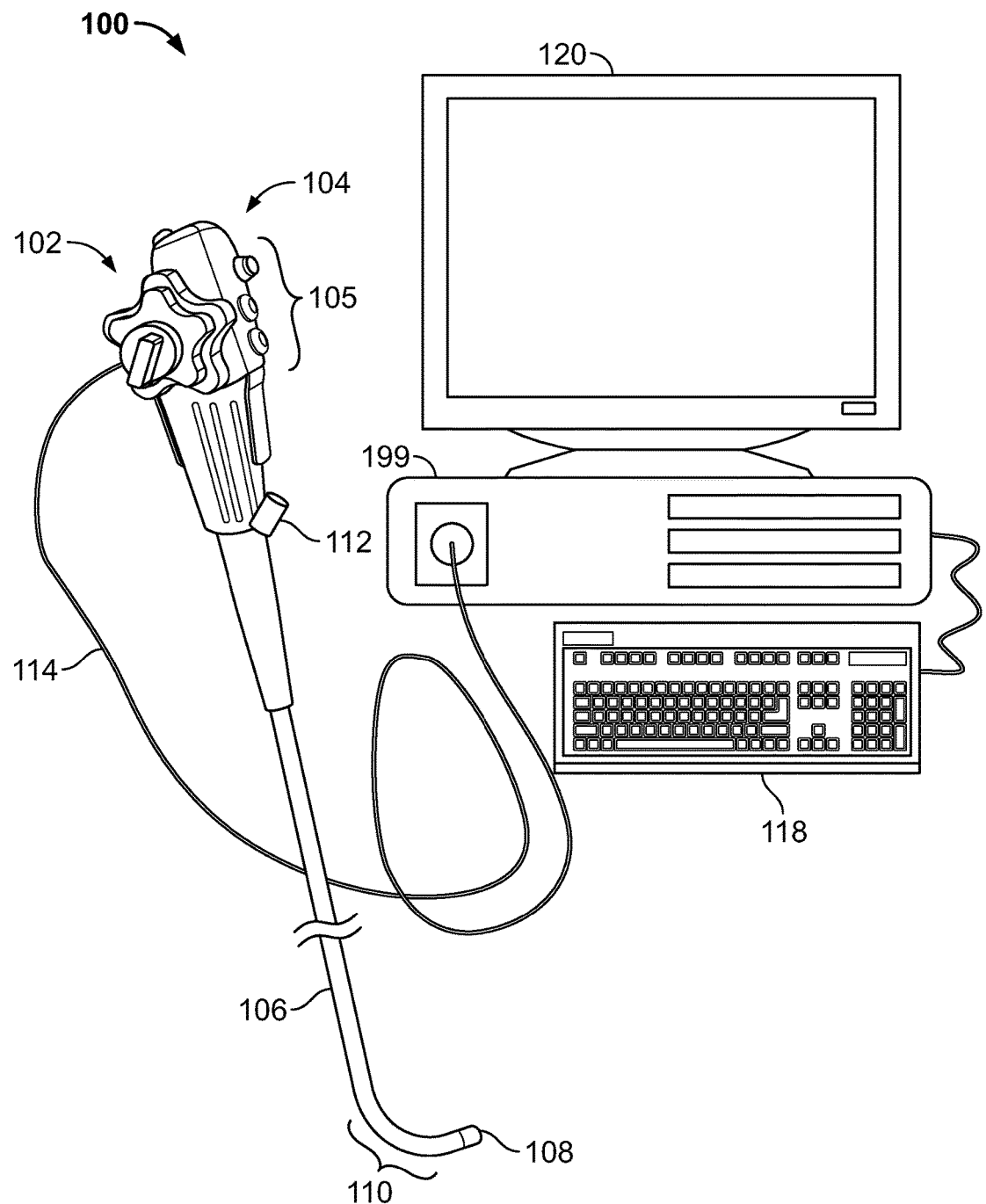
FIG. 1 illustrates an exemplary multiple viewing elements endoscopy system, as used in an embodiment of the present specification.

In one embodiment, the present specification discloses an endoscope that uses a flashing source of light, such as, but not limited to, an LED or an optical fiber light source, to provide illumination to the endoscope's viewing elements during an endoscopic procedure. In one embodiment, multiple illuminators are provided corresponding to multiple viewing elements in the tip section of the endoscope. In one embodiment, illuminators are flashed at a high intensity and for a very short duration to minimize motion blur in images caused by the movement of the endoscope. In one embodiment, flashing of the illuminators is synced with the imagers (viewing elements) to reduce interlacing artifacts.

The present specification is directed towards multiple embodiments. The following disclosure is provided in order to enable a person having ordinary skill in the art to practice the specification. Language used in this specification should not be interpreted as a general disavowal of any one specific embodiment or used to limit the claims beyond the meaning of the terms used therein. The general principles defined herein may be applied to other embodiments and applications without departing from the spirit and scope of the specification. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the specification have not been described in detail so as not to unnecessarily obscure the present specification. In the description and claims of the application, each of the words "comprise" "include" and "have", and forms thereof, are not necessarily limited to members in a list with which the words may be associated.

As used herein, the indefinite articles "a" and "an" mean "at least one" or "one or more" unless the context clearly dictates otherwise.

Embodiments of methods and/or devices of the specification may involve performing or completing selected tasks manually, automatically, or a combination thereof. Some embodiments of the specification are implemented with the use of components that comprise hardware, software, firmware or combinations thereof. In some embodiments, some components are general-purpose components such as general purpose computers or oscilloscopes. In some embodiments, some components are dedicated or custom components such as circuits, integrated circuits or software.

For example, in some embodiments, some of an embodiment is implemented as a plurality of software instructions executed by a data processor, for example, which is part of a general-purpose or custom computer. In some embodiments, the data processor or computer comprises volatile memory for storing instructions and/or data and/or a non-volatile storage, for example, a magnetic hard-disk and/or removable media, for storing instructions and/or data. In some embodiments, implementation includes a network connection. In some embodiments, implementation includes a user interface, generally comprising one or more input devices (e.g., allowing input of commands and/or parameters) and output devices (e.g., allowing reporting parameters of operation and results).

It is appreciated that certain features of the specification, which are, for clarity, described in the context of separate embodiments, may also be provided in combination in a single embodiment. Conversely, various features of the specification, which are, for brevity, described in the context of a single embodiment, may also be provided separately or in any suitable subcombination or as suitable in any other described embodiment of the specification. Certain features described in the context of various embodiments are not to be considered essential features of those embodiments, unless the embodiment is inoperative without those elements.

It is noted that the term "endoscope" as mentioned to herein may refer particularly to a colonoscope, according to some embodiments, but is not limited only to colonoscopes. The term "endoscope" may refer to any instrument used to examine the interior of a hollow organ or cavity of the body.

It should also be noted that a plurality of terms, as follows, appearing in this specification are used interchangeably to apply or refer to similar components and should in no way be construed as limiting:
  A "utility tube/cable" may also be referred to as an "umbilical tube/cable";
  A "main control unit" may also be referred to as a "controller unit", "main controller" or "fuse box";
  A "viewing element" may also be referred to as an "image capturing device/component", "viewing components", "camera", "TV camera" or "video camera";
  A "working channel" may also be referred to as a "service channel";
  An "illuminator" may also be referred to as an "illumination source", and in some embodiments, an "LED"; and
  A "flexible shaft" may also be referred to as a "bending section" or "vertebra mechanism".

Further, as used in this specification, the term "camera" is used to describe a device for capturing light. Thus, a camera, in some embodiments, comprises at least one optical lens assembly. In some embodiments, the term "camera" is used to describe an optical lens assembly and its associated image sensor. In some embodiments, the term "camera" is used to describe an optical imaging system, such as a lens assembly or assemblies and associated solid state detector arrays. In some embodiments, the terms "viewing element" and "camera" may be used interchangeably.

As used in the specification, the term "optical assembly" is used to describe a set of components that allows the endoscopic device to capture light and transform that light into at least one image. In some embodiments, lenses/optical elements are employed to capture light and image capturing devices, such as sensors, are employed to transform that light into at least one image.

Image capturing devices may be Charged Coupled Devices (CCD's) or Complementary Metal Oxide Semiconductor (CMOS) image sensors, or other suitable devices having a light sensitive surface usable for capturing an image. In some embodiments, a sensor such as a Charge Coupled Device (CCD) or a Complementary Metal Oxide Semiconductor (CMOS) image sensor (for detecting the reflected light received by an optical element), is employed.

In some embodiments, an optical element comprises a plurality of optics such as lens assemblies, lenses and protective glass, and is configured to receive reflected light from target objects.

An optical assembly, as used in the specification, comprises at least one lens assembly, its associated sensor(s), and its associated circuit board. In some embodiments, an "optical assembly" may comprise more than one viewing element or camera, associated sensor(s), and associated circuit board(s). In some embodiments, an "optical assembly" may comprise a front viewing element, its associated sensor, and its associated circuit board. In some embodiments, an "optical assembly" may comprise a front viewing element, its associated sensors, and its associated circuit board and/or at least one side viewing element, its associated sensors and its associated circuit boards. Further, the optical assembly typically is associated with at least one illuminator for illuminating the field of view. Thus, for example, a front-pointing optical assembly includes a front-pointing viewing element with associated sensor, associated circuit board and is associated with at least one illuminator.

Endoscopes that are currently being used typically have a front and side viewing elements for viewing the internal organs, illuminators, a fluid injector for cleaning the lens of the viewing elements, and sometimes also illuminators and a working channel for insertion of surgical tools. The illuminators commonly used are fiber optics that transmit light, generated remotely, to the endoscope tip section. The use of light-emitting diodes (LEDs) for illumination is also known.

A tip section of the endoscope assembly may be inserted into a patient's body through a natural body orifice, such as the mouth, nose, urethra, vagina, or anus.

In accordance with an embodiment of the present specification, a tip cover may house the tip section. The tip section, with the tip cover, may be turned or maneuvered by way of a flexible shaft, which may also be referred to as a bending section, for example, a vertebra mechanism. Tip cover may be configured to fit over the inner parts of the tip section, including an electronic circuit board assembly and a fluid channeling component, and to provide protection to the internal components in the inner parts, such as a body cavity. The endoscope can then perform diagnostic or surgical procedures inside the body cavity. The tip section carries one or more viewing elements, such as cameras, to view areas inside body cavities that are the target of these procedures.

Tip cover may include panels having a transparent surface, window or opening for optical lens assemblies of viewing elements. The panels and viewing elements may be located at the front and sides of the tip section. Optical lens assemblies may include a plurality of lenses, static or movable, providing different fields of view.

An electronic circuit board assembly may be configured to carry the viewing elements, which may view through openings on the panels. Viewing elements may include an image sensor, such as but not limited to a Charge Coupled Device (CCD) or a Complementary Metal Oxide Semiconductor (CMOS) image sensor.

The electronic circuit board assembly may be configured to carry illuminators that are able to provide illumination through illuminator optical windows. The illuminators may be associated with viewing elements, and may be positioned to illuminate the viewing elements' fields of view.

One or more illuminators may illuminate the viewing fields of the viewing elements. In an embodiment, the illuminators may be fiber optic illuminators that carry light from remote sources. The optical fibers are light carriers that carry light from a remotely located light source to the illuminators. The optical fibers extend along an insertion tube between the tip section at a distal end of the endoscope and a handle at a proximal end. An umbilical/utility tube connects the handle to a main control unit. The main control unit enables control of several functions of the endoscope assembly, including power delivered and communication of signals between the endoscope and its display, among others.

Reference is now made to FIG. 1, which shows a multiple viewing elements endoscopy system 100. System 100 may include a multiple viewing elements endoscope 102. Multiple viewing elements endoscope 102 may include a handle 104, from which an elongated shaft 106 emerges. Elongated shaft 106 terminates with a tip section 108 which is turnable by way of a bending section 110. Handle 104 may be used for maneuvering elongated shaft 106 within a body cavity. The handle may include one or more buttons and/or knobs and/or switches 105 which control bending section 110 as well as functions such as fluid injection and suction. Handle 104 may further include at least one, and in some embodiments, one or more working channel openings 112 through which surgical tools may be inserted, as well as one or more side service channel openings.

A utility cable 114, also referred to as an umbilical tube, may connect between handle 104 and a main control unit 199. Utility cable 114 may include therein one or more fluid channels and one or more electrical channels. The electrical channel(s) may include at least one data cable for receiving video signals from the front and side-pointing viewing elements, as well as at least one power cable for providing electrical power to the viewing elements and to the discrete illuminators.

The main control unit 199 contains the controls required for displaying the images of internal organs captured by the endoscope 102. The main control unit 199 may govern power transmission to the endoscope's 102 tip section 108, such as for the tip section's viewing elements and illuminators. The main control unit 199 may further control one or more fluid, liquid and/or suction pump(s) which supply corresponding functionalities to the endoscope 102. One or more input devices 118, such as a keyboard, a touch screen and the like may be connected to the main control unit 199 for the purpose of human interaction with the main control unit 199. In the embodiment shown in FIG. 1, the main control unit 199 comprises a screen/display 120 for displaying operation information concerning an endoscopy procedure when the endoscope 102 is in use. The screen 120 may be configured to display images and/or video streams received from the viewing elements of the multiple viewing elements endoscope 102. The screen 120 may further be operative to display a user interface for allowing a human operator to set various features of the endoscopy system.

Optionally, the video streams received from the different viewing elements of the multiple viewing elements endoscope 102 may be displayed separately on at least one monitor (not seen) by uploading information from the main control unit 199, either side-by-side or interchangeably (namely, the operator may switch between views from the different viewing elements manually). Alternatively, these video streams may be processed by the main control unit 199 to combine them into a single, panoramic video frame, based on an overlap between fields of view of the viewing elements. In an embodiment, two or more displays may be connected to the main control unit 199, each for displaying a video stream from a different viewing element of the multiple viewing elements endoscope 102. The main control unit 199 is described in U.S. patent application Ser. No. 14/263,896, entitled "Video Processing In A Compact Multi-Viewing Element Endoscope System" and filed on Apr. 28, 2014, which is herein incorporated by reference in its entirety.

Figure 2:
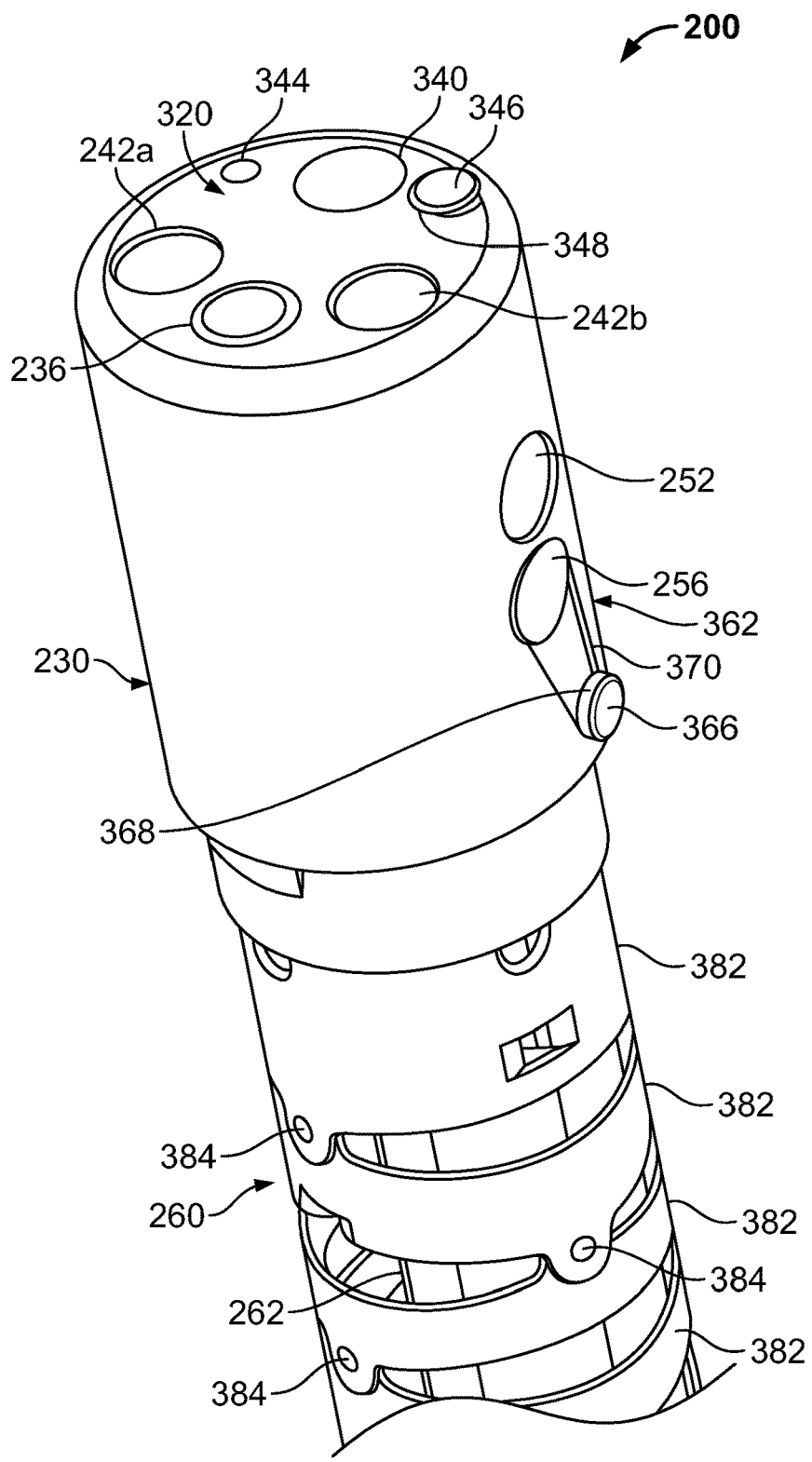
FIG. 2 schematically depicts an external isometric view of an endoscope having multiple viewing elements.

FIG. 2 schematically depicts an external isometric view of an endoscope 200 having multiple viewing elements. Referring to FIG. 2, tip 230 of endoscope 200 comprises at least a front pointing viewing element 236 and at least one side pointing viewing element 256. The viewing element may be an image sensor, such as Charge Coupled Device (CCD) or a Complementary Metal Oxide Semiconductor (CMOS) imager. Further, the term "viewing element" may generally refer to an imager and the optical system/assembly related to the imager.

In one embodiment, the front viewing element 236 is located on the front face 320 of tip 230. In one embodiment, the optical axis of the front viewing element 236 is substantially directed along the long dimension of the endoscope 200. However, since the front viewing element 236 typically has a wide angle, its Field of View (FOV) may include viewing directions at large angles relative to its optical axis. Additionally, optical windows 242a and 242b having discrete light sources such as Light Emitting Diodes (LEDs) are also seen on front face 320 of tip 230. It should be noted that number of LEDs used for illumination of the FOV may vary.

In one embodiment, distal opening 340 of working channel 262 is located on front face 320 of tip 230, such that a surgical tool inserted through working channel 262 and deployed beyond front face 320 may be viewed by the front viewing element 236. Distal opening 344 of a fluid channel may preferably also be located on front face 320 of tip 230. The fluid channel leading to distal opening 344 may be used as a jet channel for cleaning the colon.

Liquid injector 346 having a nozzle 348 aimed at front viewing element 236 is used for injecting fluid to wash contaminants such as blood, feces and other debris from front viewing element 236. Optionally, the same injector 346 is used for cleaning both front viewing element 236 and one or both optical windows 242a and 242b. Injector 346 may receive fluid (for example, water and/or gas) from the fluid channel or may be fed by a dedicated cleaning fluid channel.

Visible on the side wall 362 of tip 230 is the side pointing viewing element 256 and optical window 252 having a discrete light source such as LED. It may be noted that the number of the discrete light sources may vary. In one embodiment, optical axis of side pointing viewing element 256 may be substantially directed perpendicular to the long dimension of the endoscope 200. However, since side viewing element 256 typically has a wide angle, its field of view may include viewing directions at large angles to its optical axis.

Liquid injector 366 having a nozzle 368 aimed at side viewing element 256 is used for injecting fluid to wash contaminants such as blood, feces and other debris from the side viewing element 256. Optionally, the same injector 366 is used for cleaning both the side viewing element 256 and optical window 252. Preferably, injectors 346 and 366 are fed from same channel. An optional groove 370 helps direct the cleaning fluid from nozzle 368 towards side viewing element 256.

In the depicted embodiment, flexible shaft 260 is constructed of a plurality of links 382 connected to each other by pivots 384 Links 382 allows pushing, pulling and rotating the endoscope while pivots 384 provide limited flexibility.

The shaft 260 is preferably covered with an elastic sheath. Not seen in this figure are the electrical cables supplying power to the LEDs.

It should be noted that while only one side pointing viewing element is seen in FIG. 2, optionally, according to some embodiments, two or more side pointing viewing elements may be located within tip 230. When two side pointing viewing elements are used, they are preferably installed such that their field of views are substantially opposing. According to some embodiments, different configurations and number of side pointing viewing elements are possible and covered within the general scope of the current specification.

Figure 3:
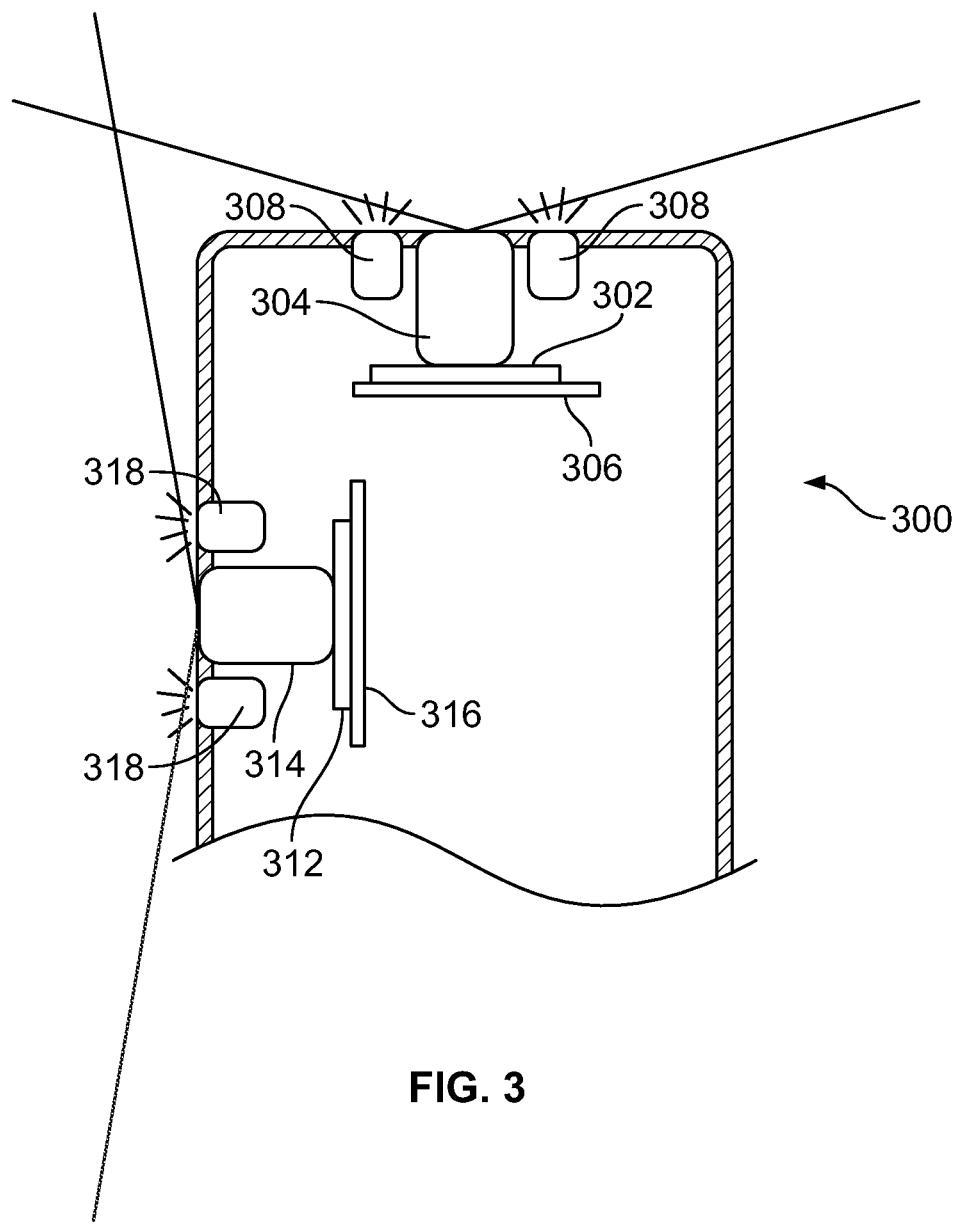
FIG. 3 shows a cross-sectional view of a tip section of a multiple viewing elements endoscope, according to some embodiments.

Reference is now made to FIG. 3, which shows a cross-sectional view of a tip section 300 of a multiple viewing elements endoscope, according to an embodiment. Tip section 300 may include a front-pointing image sensor 302, such as Charge Coupled Device (CCD) or a Complementary Metal Oxide Semiconductor (CMOS) image sensor. Front-pointing image sensor 302 may be mounted on an integrated circuit board 306, which may be rigid or flexible. Integrated circuit board 306 may supply front-pointing image sensor 302 with necessary electrical power, and may derive still images and/or video feeds captured by the image sensor 302. Integrated circuit board 306 may be connected to a set of electrical cables (not shown) which may be threaded through an electrical channel running through the elongated shaft of the endoscope. Front-pointing image sensor 302 may have a lens assembly 304 mounted on top of it and providing the necessary optics for receiving images. Lens assembly 304 may include a plurality of lenses, static or movable, which may provide a field of view of at least 90 degrees and up to essentially 180 degrees. Front-pointing image sensor 302 and lens assembly 304, with or without integrated circuit board 306, may be jointly referred to as a "front pointing viewing element".

One or more discrete front illuminators 308, such as LEDs, may be placed next to lens assembly 304, for illuminating its field of view. Optionally, discrete front illuminators 308 may be attached to the same integrated circuit board 306 on which front-pointing image sensor 302 is mounted (this configuration is not shown).

Tip section 300 may further include a side-pointing image sensor 312, such as Charge Coupled Device (CCD) or a Complementary Metal Oxide Semiconductor (CMOS) image sensor. Side-pointing image sensor 312 may be mounted on an integrated circuit board 316, which may be rigid or flexible. Integrated circuit board 316 may supply side-pointing image sensor 312 with necessary electrical power, and may derive still images and/or video feeds captured by the image sensor 312. Side-pointing image sensor 312 may have a lens assembly 314 mounted on top of it and providing the necessary optics for receiving images. Side-pointing image sensor 312 and lens assembly 314, with or without integrated circuit board 316, may be jointly referred to as a "side pointing viewing element".

One or more discrete side illuminators 318, such as LEDs, may be placed next to lens assembly 314, for illuminating its field of view. Optionally, discrete side illuminators 318 may be attached to the same integrated circuit board 316 on which side-pointing image sensor 312 is mounted (this configuration is not shown).

In another configuration (not shown), integrated circuit boards 306 and 316 may be a single integrated circuit board on which both front and side-pointing image sensors 302 and 312 are mounted. Front and side-pointing image sensors 302 and 312 may be similar or identical in terms of, for example, field of view, resolution, light sensitivity, pixel size, focal length, focal distance and/or the like. Further, there may be two side-pointing image sensors, as described above.

According to some embodiments, white light LEDs may be used to illuminate the fields of view. According to other embodiments, other colors of LEDs or any combination of LEDs may be used (for example, red, green, blue, infrared, ultraviolet). It should be noted that number of LED light sources and their position in respect to the image sensors may vary within the scope of the current specification.

When light is continuously emitted from an illuminator during an endoscopic procedure, it leads to blurred or fuzzy images, especially during fast movement of the scope. Further, the longer the exposure, the fuzzier the images. For example, an exposure of $\frac{1}{60}^{th}$ second can lead to fuzzy images in the colon on fast movement of the scope. It may be obvious to one of ordinary skill in the art that still image capture, as well as HD video, is meant to help identify fine details in the endoscopic image. Motion blur that makes for a smooth video can hide such fine details and significantly reduce the still image quality.

Figure 4:
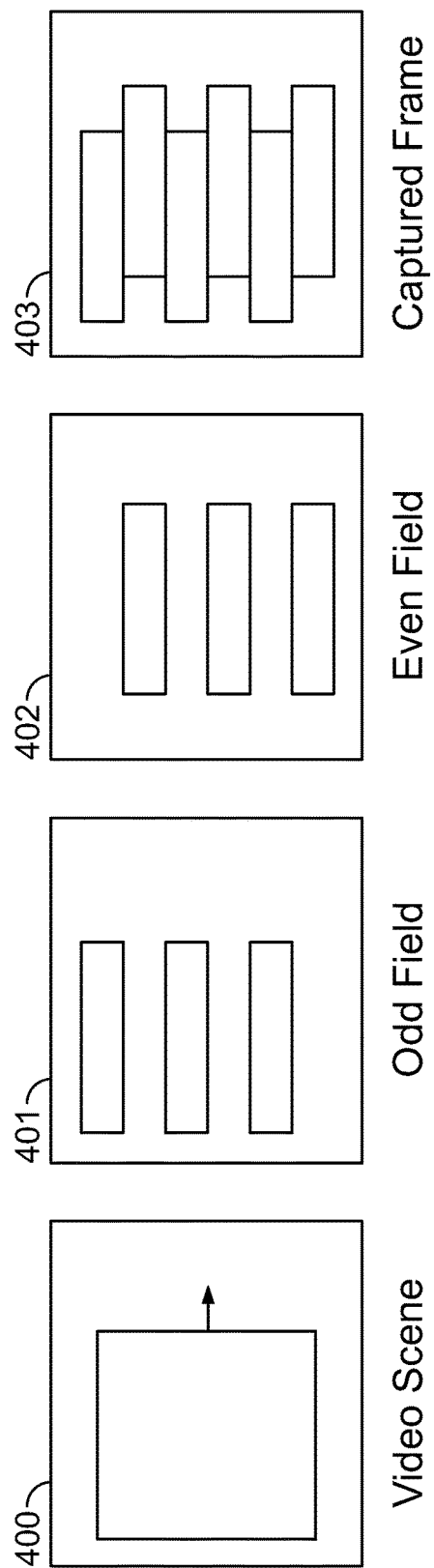
FIG. 4 illustrates artifacts in an interlaced video.

In addition, due to movement of the scope, video tends to suffer from interlacing artifacts. It is known in the art that in interlaced video, two interlaced fields, each with a vertical resolution of half an image taken at different points in time relative to each other, are captured and combined together as a single frame of a full image size. In this resulting frame, even numbered horizontal lines belong to one field, while odd numbered lines belong to the other field. This is shown in FIG. 4. Referring to FIG. 4, screen 401 represents the field with odd numbered lines and screen 402 represents the field with even numbered lines of the video scene 400. Generally, the time difference between the capture of odd and even fields is very short, typically on the order of $\frac{1}{60}^{th}$ of a second. However, if there is movement of the imaging sensor or viewing element during the short time difference between the two fields, the two half-images will be different than each other, and the movement will appear as artifacts. These artifacts can be seen as misfit or incongruous horizontal lines in screen 403.

The phenomena of fuzzy images and interlacing artifacts due to scope movement is a factor contributing to certain problems, such as the hit miss rate (12-24%) of polyps during colonoscopy. Missing polyps, or a "false negative" diagnosis, may result in late discovery of cancer.

The present specification addresses the above problems by flashing the illuminators or light sources (LEDs) to produce frozen and non-fuzzy images, as opposed to using continuous light. In one embodiment, the LEDs are flashed at high intensity for a very short duration. Shorter exposure to light leads to less movement being captured per image and thus, less fuzziness. In general, a shorter interval of the order of $\frac{1}{125}$ sec to $\frac{1}{250}$ sec significantly decreases blur. In one embodiment, LEDs are flashed for a duration of about $\frac{1}{250}^{th}$ of a second, resulting in a viewing element flash-like lighting. In another embodiment, LEDs are flashed for a duration of between $\frac{1}{75}^{th}$ of a second to $\frac{1}{350}^{th}$ of a second, and any increment therein, wherein the flash rate is optimized to be the slowest flash rate that still produces an artifact or blur free image.

The systems and methods of the present specification operate under two main assumptions. The first is that the entire field is integrating at the same time, for example, using a global shutter or CMOS flash mode (pulsed exposure mode), but not a CMOS rolling shutter. The second assumption is that in the case of interlaced images, different fields are integrating in mutually exclusive times (for example, the odd field first, and then the even field or vice versa). Motion blur is reduced or eliminated by shortening the amount of time light hits the entire scene. Therefore, in various embodiments the flash length is shorter than the integration length per field and as long as needed to still provide enough light to avoid generating noise.

In one embodiment, the present specification enables manual activation of a single flash to capture a still image and freeze its fine detail. This may be done, for example, by pressing a button on the endoscope's handle. Such buttons are shown as 105 in FIG. 1. Thus, pressing a button on the scope handle results in an image capture along with a flash of the illuminating LEDs. In one embodiment, LEDs remain off unless flashed or activated.

Figure 5:
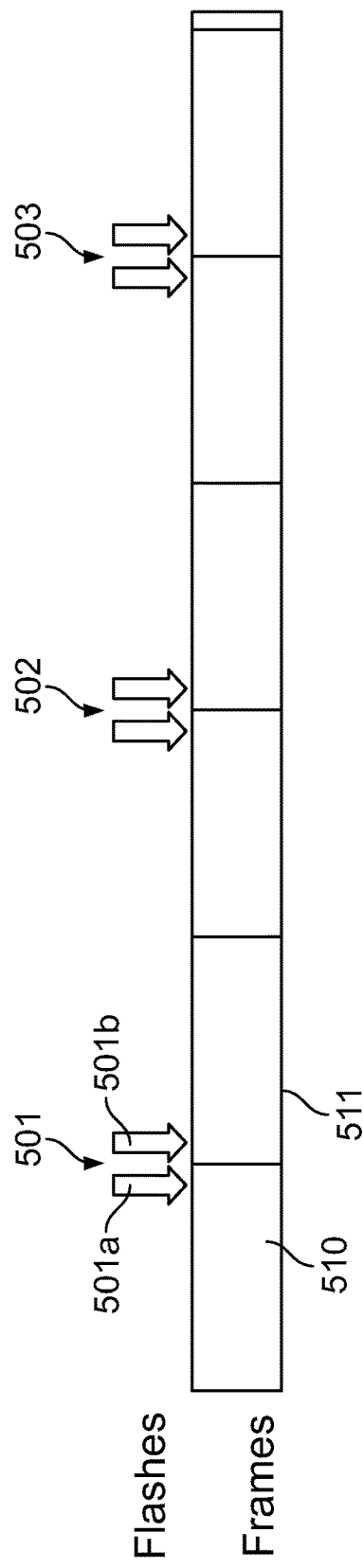
FIG. 5 illustrates flashing of LEDs to reduce interlacing artifacts, according to one embodiment.

In another embodiment, to address artifacts in interlaced video, LEDs are flashed at the end of the image capture corresponding to the first field and then at the start of the image capture of the second field. This results in a very short time difference between the captured fields of an interlaced image. FIG. 5 illustrates this method. Referring to FIG. 5, a series of consecutive pairs of flashes 501, 502 and 503 can be seen. The first flash 501*a* in consecutive pair of flashes 501 is fired just before the end of the field 510, while the second flash 501*b* is fired just after the beginning of the field 511. Similarly, other pairs of consecutive flashes are timed to be fired towards the end and beginning of consecutive fields. In one embodiment, the timing of flashes is synced with the imager. Thus, LEDs are activated as a series of short flashes in a stroboscopic effect that is synced with the video capture frame-rate to get better fine detail in video. Thus, for example, if the LEDs are flashed at a frequency of 60 Hz, in sync with the imager, it would result in images (video) at a frequency of 30 Hz, since two fields captured at 60 Hz are combined to form a single frame image of 30 Hz. The resulting images would display minimal interlacing artifacts, and would simplify post-processing of the images.

In various embodiments, wherein the image is interlaced having a first integration field and a second integration field to create a single interlaced frame, a first flash is delayed to begin toward the end of the first integration field's integration time and a second flash is advanced to begin toward the beginning of the second integration field's integration time. In one embodiment, wherein the single interlaced frame is 1/30 sec and comprises a 1/60 sec first integration frame and a 1/60 sec second integration frame, the first flash is about 1/125 sec, beginning about 1/125 sec after the first integration field starts and ending when the first integration field ends. The second flash is also about 1/125 sec, beginning when the second integration field starts and ending about 1/125 sec after said start of said second integration field. Therefore, in said embodiment, the first flash coincides with approximately the second half, or 50%, of the first integration field integration time and the second flash coincides with approximately the first half, or 50%, of the second integration field integration time.

In another embodiment, each flash duration is reduced to about 1/250 sec and the first and second flash times are still set to coincide with the end of the first integration field and the beginning of the second integration field respectively. Therefore, for a single interlaced frame of 1/30 sec comprising a 1/60 sec first integration frame and a 1/60 sec second integration frame, the first approximately 1/250 sec flash begins about 1/250 before the first integration field ends and ends with said first integration field, and the second approximately 1/250 flash begins with said second integration field and ends about 1/250 sec after the second integration field starts. In this embodiment, the first flash coincides with approximately the last 25% of the first integration field and the second flash coincides with approximately the first 25% of the second integration field, leaving approximately 75% of each field flash free.

Though embodiments having first and second integration fields of 1/60 sec and first and second flashes of approximately 1/125 or 1/250 sec have been described, additional embodiments having varying integration field lengths and flash durations are envisioned. In various embodiments, for example, the integration fields have lengths ranging from approximately 1/120 sec to approximately 1/30 sec and the flashes have durations ranging from approximately 1/1000 sec to approximately 1/60 sec, and every increment therein. Additionally, in various embodiments, the flashes have durations ranging from approximately 75% of their respective integration field to 5% of their respective integration field and every percentage increment therein.

It may be noted that interlacing artifacts are minimized in the present specification by making the two fields appear similar by reducing the time difference between them. This is achieved by exposing the earlier field to a short flash at the end of its exposure time, while exposing the later field to a short flash at the beginning of its exposure time, resulting in an apparent reduction in the time difference between the captured scenes in the two fields. This is in contrast to various other 'de-interlacing' methods used in prior art methods to address the problem of interlaced artifacts. Some of these prior art de-interlacing methods reduce resolution, while others require significant processing. The method of the present specification simplifies the solution for minimizing image artifact by achieving higher similarity between neighboring fields.

Figure 6:
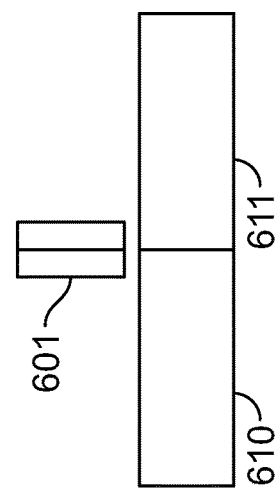
FIG. 6 illustrates flashing of LEDs to reduce interlacing artifacts, according to another embodiment.

In another embodiment, shown in FIG. 6, instead of consecutive flashes at the end and beginning of consecutive fields, a longer LED flash 601 is used that runs just before the end of a first field 610 to just after the start of the next field 611. Referring to FIG. 6, LED flash 601 starts towards the end of field 610 and continues up through the beginning of field 611. In one embodiment, flash 601 is illuminated for $1/60^{th}$ of a second which covers the second half of the early field and first half of the later field, and is pulsed at a frequency of 30 Hz.

In various embodiments, wherein the image is interlaced having a first integration field and a second integration field to create a single interlaced frame, a single flash is delayed to begin toward the end of the first integration field's integration time and end toward the beginning of the second integration field's integration time. The duration of the single flash is configured to comprise equal portions of the first integration field and the second integration field. In one embodiment, wherein the single interlaced frame is 1/30 sec and comprises a 1/60 sec first integration frame and a 1/60 sec second integration frame, the flash is 1/60 sec, beginning 1/125 sec after the first integration field starts and ending 1/125 sec before the second integration field ends. Therefore, in said embodiment, the flash coincides with approximately the second half, or 50%, of the first integration field integration time and approximately the first half, or 50%, of the second integration field integration time.

In another embodiment, the flash duration is reduced to 1/125 sec and the flash time is still set to coincide with the end of the first integration field and the beginning of the second integration field. Therefore, for a single interlaced frame of 1/30 sec comprising a 1/60 sec first integration frame and a 1/60 sec second integration frame, the 1/125 sec flash begins 1/250 before the first integration field ends and ends 1/250 sec after the second integration field starts. In this embodiment, the flash coincides with approximately the last 25% of the first integration field and the first 25% of the second integration field, leaving approximately 75% of each field flash free.

Though embodiments having first and second integration fields of 1/60 sec and flashes of 1/60 or 1/125 sec have been described, additional embodiments having varying integration field lengths and flash durations are envisioned. In various embodiments, for example, the integration fields have lengths ranging from 1/120 sec to 1/30 sec and the flashes have durations ranging from 1/1000 sec to 1/30 sec, and every increment therein. Additionally, in various embodiments, the flashes have durations ranging from approximately 75% of their respective integration field to 5% of their respective integration field and every percentage increment therein.

It may be noted that using a single flash from the end of one field to the beginning of the next field has the same effect as using a pair of consecutive flashes and reduces the time difference between the captured images in the two fields to minimize interlacing artifacts.

It may be noted that the duration of an LED flash needs to be short enough to cover only part of the exposure time of each field in order to reduce fuzziness and maintain fine detail in images. For example, if a single field exposure time is $1/60^{th}$ of a second, then a flash of about $1/125^{th}$ of a second is a good start per field. In general, for exposure intervals on the order of 1/60 sec to 1/30 sec, flash intervals for reducing blurriness are in the range of 1/125 sec to 1/250 sec, or shorter.

It may be noted that in the present specification, automatic and constant flashing at a pre-determined frequency may be used to minimize interlacing artifacts in video images. Additionally, the techniques of the present specification may also be applied to capture individual still images that have better sharpness and detail. For this purpose, an LED flash may be activated manually while capturing a still image, as explained earlier. In one embodiment, two interlaced fields are captured, each capture being accompanied by a flash of LEDs, and the captured fields are then combined into a single still frame. This technique results in a still image with fine detail and can be used when the physician requires a single frame capture.

Figure 7:
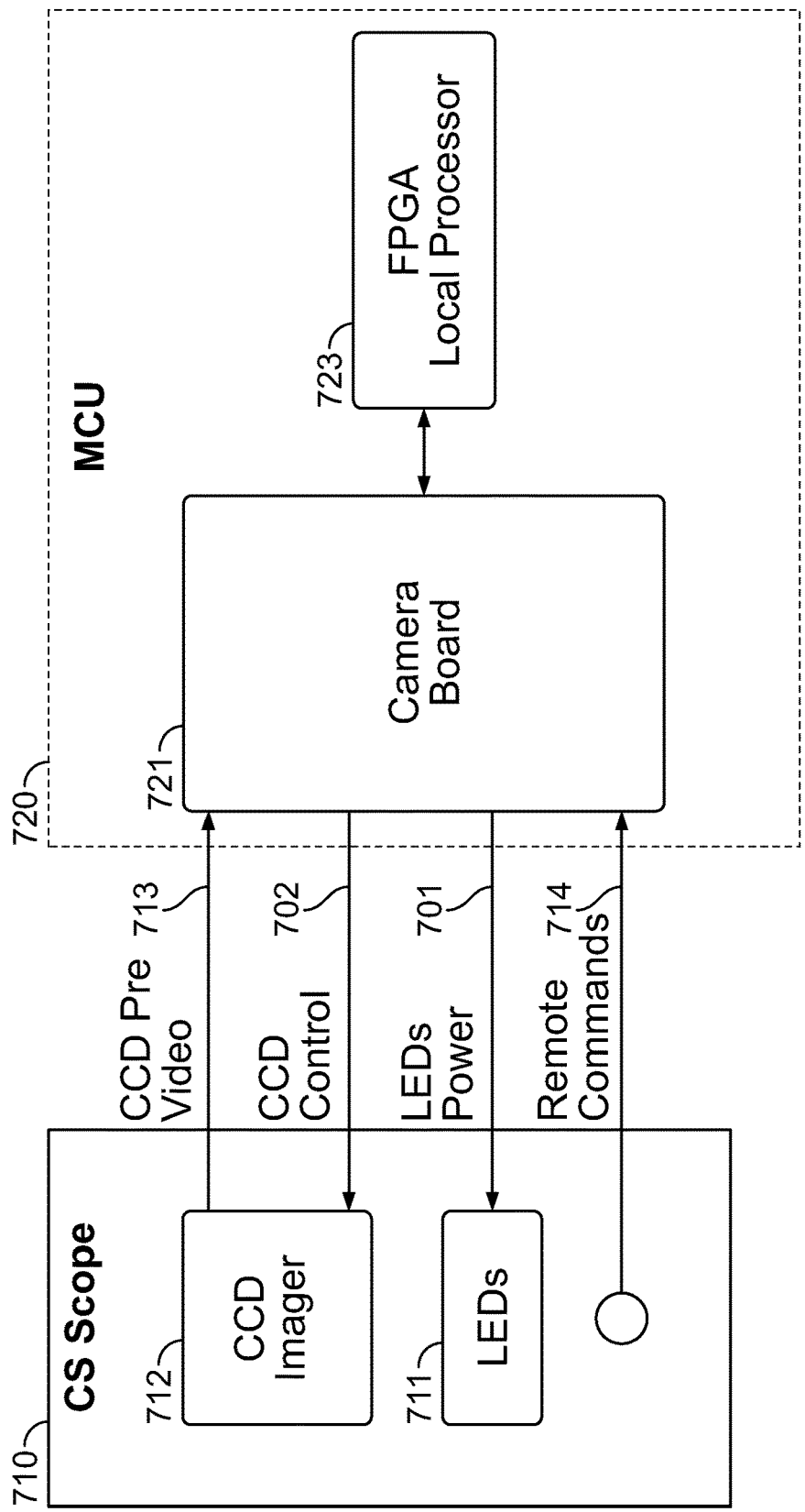
FIG. 7 is a block diagram illustrating the control hardware for a multiple viewing elements endoscopy system, according to one embodiment of the present specification.

FIG. 7 details how a controller 720, also known as MCU (Main Controller Unit) operatively connects with the image sensors 712 and illuminators 711 in endoscope 710. Referring to FIG. 7, controller 720 further comprises a camera board 721 that controls the power supplies 701 to the LEDs 711 and transmits controls 702 for the operation of image sensor(s) 712 in the endoscope 710. In one embodiment, LEDs 711, which are used for illuminating the fields of view of corresponding sensors, receive power separately and individually. Therefore, in a case of three image sensors, there are three LED circuits for illumination and correspondingly, three signals for power voltages. In one embodiment, image sensor 712 may be a Charge Coupled Devices (CCD) or a Complementary Metal Oxide Semiconductor (CMOS) imager. The camera board 721 in turn receives video signal(s) 713 generated by the CCD imager 712 and also other remote commands 714 from the endoscope 710. In one embodiment, remote commands include the command for still image capture with LED flash, which is generated when the user presses a designated button on the endoscope. In one embodiment, pressing a designated button for still image capture results in capture of two interlaced fields, each accompanied by flash, which are then combined into a single still image frame. These commands are executed by the camera board to control the operation of image sensors and LEDs.

Camera board 721 is in communication with an FPGA (Field Programmable Gate Array) 723, which is a logic device programmed specifically for system requirements. FPGA 723 performs tasks that may be categorized in two types: logic tasks which must be implemented by hardware (as opposed to software), and logic tasks related to video image processing. Thus, FPGA 723 may be programmed to flash the LEDs 711 for illumination at a pre-set frequency and for a pre-determined duration to eliminate interlacing artifacts as explained above. The pre-programmed instructions from the FPGA 723 are executed by the camera board 721 to control the power supplied to the LEDs 711.

Controller 720 further comprises elements (not shown) for processing the video obtained from the image sensors 712 through the camera-board 721, as well as other elements for system monitoring and control.

In various embodiments, the flash frequency, intensity, and duration are fine-tuned based on the amount of image blur, noise, and temperature generated. The frequency is set to match the beginning and ending of first and second integration frames, as described above. For example, for embodiments having two flashes per single interlaced frame, a first flash is set to begin toward the end of a first integration frame and end with said first integration frame while a second flash is set to begin with a second integration frame and end after the beginning of said second integration frame. Subsequent pairs of flashes are set to have the same frequency with respect to following pairs of integration frames. For embodiments having a single flash per single interlaced frame, a single flash is set to begin toward the end of a first integration frame and end after the beginning of a second integration frame. Subsequent single flashes are set to have the same frequency with respect to following pairs of integration frames.

Regarding flash duration, shorter flashes result in less image blur but more noise, or variation of image brightness or color information, while conversely, longer flashes result in more image blur with less noise. A higher flash intensity results in less image noise but higher temperatures, or intensity of image colors.

Figure 8A:
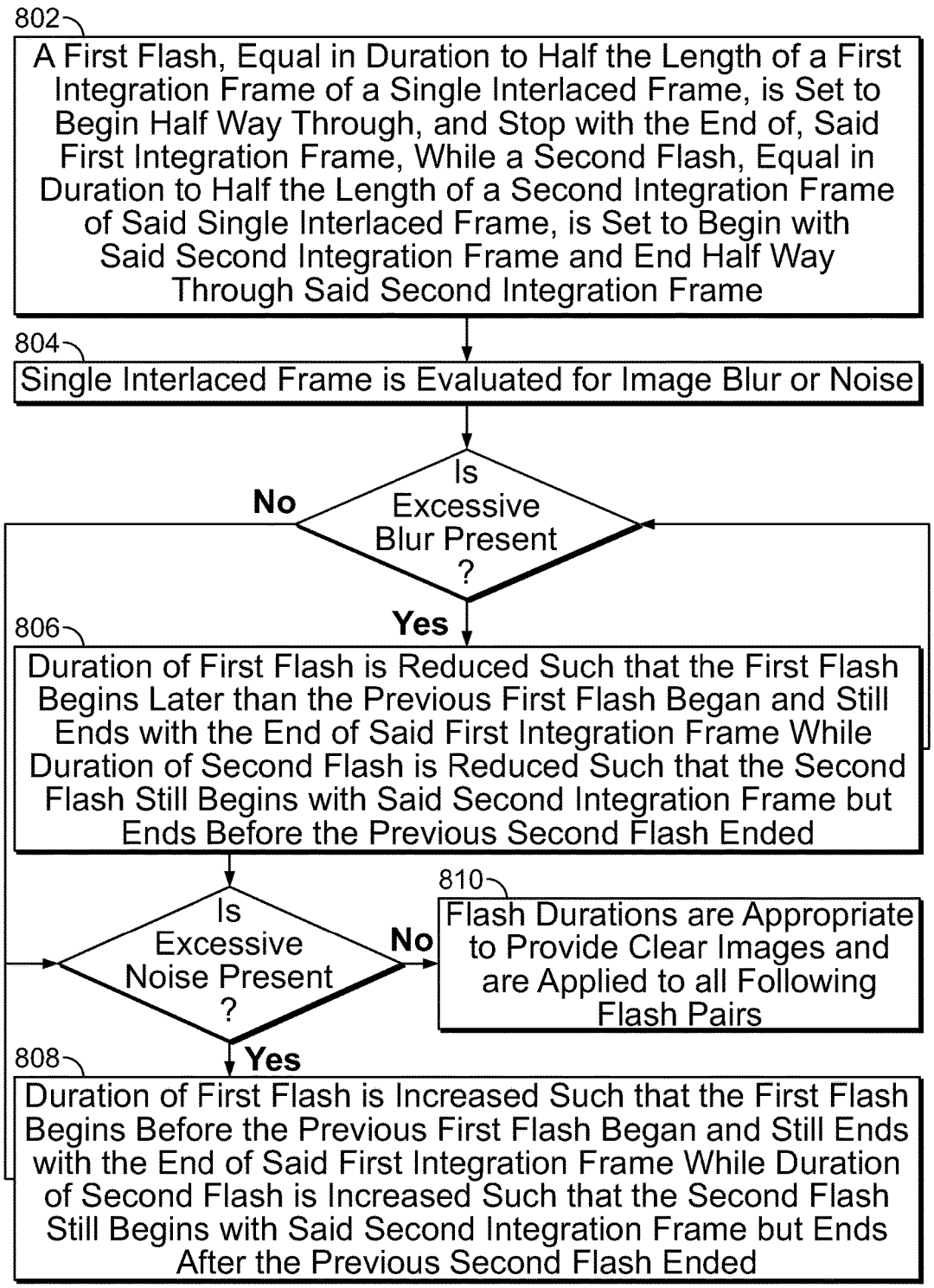
FIG. 8A is a flowchart listing the steps involved in one embodiment of fine tuning the duration of each flash in a pair of flashes with respect to a pair of integration frames.

FIG. 8A is a flowchart listing the steps involved in one embodiment of fine tuning the duration of each flash in a pair of flashes with respect to a pair of integration frames. At step 802, a first flash, equal in duration to half the length of a first integration frame of a single interlaced frame, is set to begin half way through, and stop with the end of, said first integration frame, while a second flash, equal in duration to half the length of a second integration frame of said single interlaced frame, is set to begin with said second integration frame and end half way through said second integration frame. The single interlaced image generated by the two integration frames is evaluated for image blur or noise at step 804. If excessive blur is present, at step 806, the duration of first flash is reduced such that the first flash begins later than the previous first flash began and still ends with the end of said first integration frame, while the duration of the second flash is reduced such that the second flash still begins with said second integration frame but ends before the previous second flash ended. If excessive blur is still present, step 806 can be repeated to further reduce the duration of the flashes. If the image contains no excessive blur or the blur has been eliminated by reducing the flash duration at step 806, but the image contains excessive noise, then, at step 808, the duration of the first flash is increased such that the first flash begins before the previous first flash began and still ends with the end of said first integration frame, while the duration of the second flash is increased such that the second flash still begins with said second integration frame but ends after the previous second flash ended. If excessive noise is still present, step 808 can be repeated to further increase the duration of the flashes. If the image contains no excessive blur or noise, or excessive blur or noise has been eliminated by reducing or increasing the flash duration at steps 806 or 808 respectively, then the flash durations are appropriate to provide clear images and are applied to all following flash pairs at step 810. In various embodiments, step 808 of increasing flash duration to eliminate noise may be performed prior to step 806 of reducing flash duration to eliminate blur.

Figure 8B:
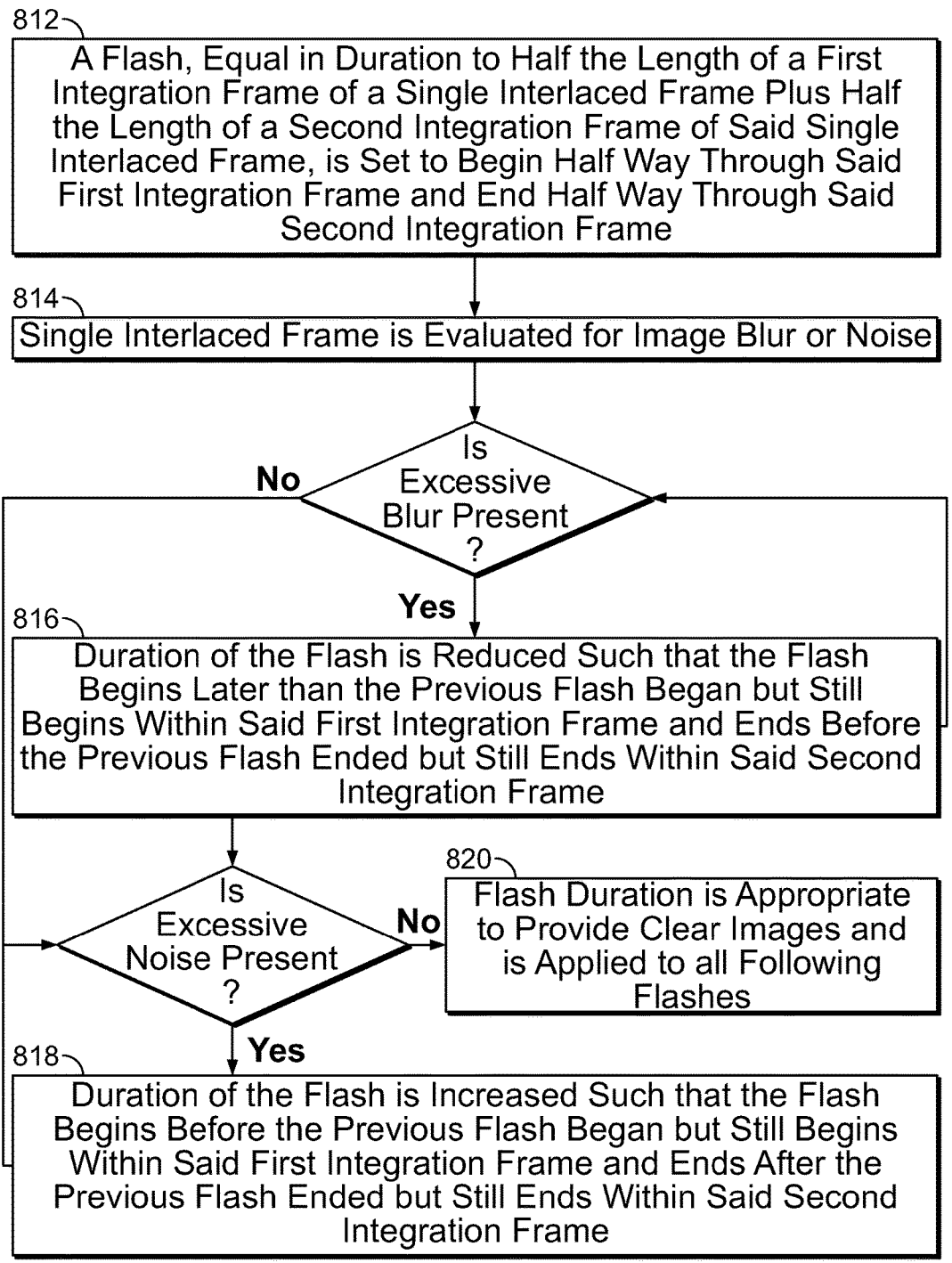
FIG. 8B is a flowchart listing the steps involved in one embodiment of fine tuning the duration of a single flash with respect to a pair of integration frames.

FIG. 8B is a flowchart listing the steps involved in one embodiment of fine tuning the duration of a single flash with respect to a pair of integration frames. At step 812, a flash, equal in duration to half the length of a first integration frame of a single interlaced frame plus half the length of a second integration frame of said single interlaced frame, is set to begin half way through said first integration frame and end half way through said second integration frame. The single interlaced image generated by the two integration frames is evaluated for image blur or noise at step 814. If excessive blur is present, at step 816, the duration of the flash is reduced such that the flash begins later than the previous flash began but still begins within said first integration frame and ends before the previous flash ended but still ends within said second integration frame. If excessive blur is still present, step 816 can be repeated to further reduce the duration of the flash. If the image contains no excessive blur or the blur has been eliminated by reducing the flash duration at step 816, but the image contains excessive noise, then, at step 818, the duration of the flash is increased such that the flash begins before the previous flash began but still begins within said first integration frame and ends after the previous flash ended but still ends within said second integration frame. If excessive noise is still present, step 818 can be repeated to further increase the duration of the flash. If the image contains no excessive blur or noise, or excessive blur or noise has been eliminated by reducing or increasing the flash duration at steps 816 or 818 respectively, then the flash duration is appropriate to provide clear images and is applied to all following flashes at step 820. In various embodiments, step 818 of increasing flash duration to eliminate noise may be performed prior to step 816 of reducing flash duration to eliminate blur.

The above examples are merely illustrative of the many applications of the system of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

I claim:

1. A method of reducing blur and noise in an image generated by an endoscope system, comprising the steps of:
   providing an endoscope system comprising an endoscope having a tip;
   one or more viewing elements positioned in said tip, wherein each viewing element comprises an image sensor and lens assembly;
   one or more discrete illuminators positioned in said tip to illuminate the fields of view of said viewing elements; and
   a controller external to said endoscope for concurrently controlling the viewing elements and the illuminators, wherein the controller is configured to flash the illuminators in a pair of flashes, each flash of the pair of flashes having a pre-set duration relative to a single interlaced image frame comprising a first integration frame having a first length, a first beginning, and a first end, and a second integration frame having a second length, a second beginning, and a second end, wherein a first flash of said pair of flashes is configured to have a first pre-set duration beginning after said first beginning and ending at said first end of said first integration frame and being shorter than said first length of said first integration frame, and wherein a second flash of said pair of flashes is configured to have a second pre-set duration beginning at said second beginning and ending before said second end of said second integration frame and being shorter than said second length of said second integration frame;
   setting said first pre-set duration of said first flash to a fraction of said first length to begin part way through said first integration frame and end at said first end of said first integration frame, and setting said second pre-set duration of said second flash to a fraction of said second length to begin at said second beginning and end part way through said second integration frame;
   evaluating said single interlaced image frame for blur;
   reducing said first pre-set duration such that said first flash begins later than the previous first flash began and still ends at the end of said first integration frame, and reducing said second pre-set duration such that said second flash still begins with said second integration frame but ends before the previous second flash ended to reduce or eliminate blur;
   re-evaluating said single interlaced image frame for noise;
   increasing said first pre-set duration such that said first flash begins before the previous first flash began and still ends at the end of said first integration frame, and increasing said second pre-set duration such that said second flash still begins with said second integration frame but ends after the previous second flash ended to reduce or eliminate noise; and
   applying said first pre-set duration to all following first flashes and said second pre-set duration to all following second flashes once blur and noise have been satisfactorily reduced or eliminated to be within a predetermined range.

2. The method of claim 1, wherein the one or more discrete illuminators comprise light emitting diodes (LEDs).

3. The method of claim 1, wherein the one or more discrete illuminators comprise optic fibers.

4. The method of claim 1, wherein the one or more discrete illuminators comprise at least two discrete illuminators, and wherein the at least two illuminators comprise a combination of light emitting diodes (LEDs) and optical fibers.

5. The method of claim 1, wherein the first length of the first integration frame and the second length of the second integration frame each ranges from approximately $\frac{1}{120}$ of a second to $\frac{1}{30}$ of a second.

6. The method of claim 1, wherein the first pre-set duration of the first flash and the second pre-set duration of the second flash each ranges from approximately $\frac{1}{1000}$ of a second to $\frac{1}{60}$ of a second.

7. The method of claim 1, wherein the first length of the first integration frame and the second length of the second integration frame are each equal to approximately $\frac{1}{60}$ of a second, and the first pre-set duration of the first flash and the second pre-set duration of the second flash are each equal to approximately $1/125$ of a second.

8. The method of claim 1, wherein the endoscope further comprises a handle with buttons for controlling functions of the endoscope and the controller; and wherein a button on the endoscope handle may be pressed to flash the one or more discrete illuminators.

9. The method of claim 1, wherein the controller comprises:
   a camera board for controlling power supply to the one or more discrete illuminators and controlling the operation of the image sensors of the viewing elements; and
   a field programmable gate array (FPGA) in communication with the camera board for performing logical tasks implemented by hardware and logical tasks related to video image processing.

* * * * *